US00PP19573P2

(12) United States Plant Patent
Stöckmann et al.

(10) Patent No.: US PP19,573 P2
(45) Date of Patent: Dec. 16, 2008

(54) ***ILEX* PLANT NAMED 'CASANOVA'**

(50) Latin Name: *Ilex meserveae*
Varietal Denomination: Casanova

(75) Inventors: Ernst Adolf Stöckmann, Westersteder Strasse 20a, D-26160, Bad Zwischenahn (DE); Friedrich Renken, Jaderberg (DE)

(73) Assignee: Ernst Adolf Stöckmann, Bad Zwischenahn (DE)

( * ) Notice: Subject to any disclaimer, the term of this patent is extended or adjusted under 35 U.S.C. 154(b) by 0 days.

(21) Appl. No.: 12/011,391

(22) Filed: Jan. 25, 2008

(51) Int. Cl.
*A01H 5/00* (2006.01)

(52) U.S. Cl. ..... Plt./247

(58) Field of Classification Search ..... Plt./247
See application file for complete search history.

*Primary Examiner*—Annette H Para
(74) *Attorney, Agent, or Firm*—C. A. Whealy

(57) ABSTRACT

A new and distinct cultivar of *Ilex* plant named 'Casanova', characterized by its upright and outwardly spreading plant habit; freely branching habit; dark green and pale yellow bi-colored foliage; dark red-colored stems; red-colored flower buds; and good garden performance.

2 Drawing Sheets

Botanical designation: *Ilex meserveae.*
Cultivar denomination: 'Casanova'.

BACKGROUND OF THE INVENTION

The present Invention relates to a new and distinct cultivar of *Ilex,* botanically known as *Ilex meserveae,* and hereinafter referred to by the name 'Casanova'.

The new *Ilex* is a naturally-occurring branch mutation of the *Ilex meserveae* cultivar Blue Prince, not patented. The new *Ilex* was discovered and selected by the Inventors from with a population of plants of the cultivar Blue Prince in a controlled environment in Westerstede, Germany in 1993.

Asexual reproduction of the new *Ilex* by cuttings taken in a controlled environment in Bad Zwischenahn, Germany since 1994 has shown that the unique features of this new *Ilex* are stable and reproduced true to type in successive generations.

SUMMARY OF THE INVENTION

The new *Ilex* has not been observed under all possible environmental conditions. The phenotype may vary somewhat with variations in environment such as temperature and/or light intensity without, however, any variance in genotype. The following traits have been repeatedly observed and are determined to be the unique characteristics of 'Casanova'. These characteristics in combination distinguish 'Casanova' as a new and distinct cultivar of *Ilex:*

1. Upright and outwardly spreading plant habit.
2. Freely branching habit.
3. Dark green and pale yellow bi-colored foliage.
4. Dark red-colored stems.
5. Red-colored flower buds.
6. Good garden performance.

Plants of the new *Ilex* differ from plants of the parent, the cultivar Blue Prince, in the following characteristics:

1. Plants of the new *Ilex* are slower-growing than plants of the cultivar Blue Prince.

2. Plants of the new *Ilex* have green and pale yellow bi-colored foliage whereas plants of the cultivar Blue Prince have dark green-colored foliage.

Plants of the new *Ilex* can be compared to the plants of the *Ilex meserveae* cultivar Blue Angel, not patented. In side-by-side comparisons conducted in Boskoop, The Netherlands, plants of the new *Ilex* differed from plants of the cultivar Blue Angel in the following characteristics:

1. Plants of the new *Ilex* were more compact than and not as upright as plants of the cultivar Blue Angel.
2. Plants of the new *Ilex* had green and pale yellow bi-colored foliage whereas plants of the cultivar Blue Angel had green-colored foliage.
3. Plants of the new *Ilex* did not produce berries whereas plants of the cultivar Blue Angel produced red-colored berries.

BRIEF DESCRIPTION OF THE PHOTOGRAPHS

The accompanying colored photographs illustrate the overall appearance of the new *Ilex.* These photographs show the colors as true as it is reasonably possible to obtain in colored reproductions of this type. Colors in the photographs may differ slightly from the color values cited in the detailed botanical description, which accurately describe the colors of the new *Ilex.*

The photograph on the first sheet comprises a side perspective view of a typical plant of 'Casanova' grown in a container.

The photograph at the top of the second sheet is a close-up view of typical leaves of 'Casanova'.

The photograph at the bottom of the second sheet is a close-up view of typical flower buds and flowers of 'Casanova'.

DETAILED BOTANICAL DESCRIPTION

The aforementioned photographs and following observations and measurements describe plants grown in Boskoop, The Netherlands in 19-cm containers, in an outdoor nursery during the winter and under commercial production conditions. During the production of the plants, day temperatures ranged from 1° C. to 12° C. and night temperatures ranged from −5° C. to 5° C. Plants used for the photographs and description were about five years old. In the following description, color references are made to The Royal Horticultural Society Colour Chart, 2001 Edition, except where general terms of ordinary dictionary significance are used.

Botanical classification: *Ilex meserveae* 'Casanova'.

Parentage: Naturally-occurring branch mutation of the *Ilex meserveae* cultivar Blue Prince, not patented.

Propagation:

*Type.*—By cuttings.

*Time to produce a rooted young plant, summer.*—About two months at temperatures of 20° C. to 30° C.

*Time to produce a rooted young plant, winter.*—About three months at temperatures of 15° C. to 25° C.

*Root description.*—Thick, fleshy; white in color.

*Rooting habit.*—Moderate branching; moderately dense.

Plant description:

*Plant form and growth habit.*—Perennial evergreen shrub; upright and outwardly spreading plant habit; globular to broadly inverted triangle. Low vigor.

*Branching habit.*—Freely branching habit; about three primary lateral branches and about 46 secondary lateral branches developing per plant.

*Plant height.*—About 37 cm.

*Plant diameter, area of spread.*—About 41 cm.

*Lateral branch description.*—Length: About 11.3 cm. Diameter: About 3.5 mm. Internode length: About 8 mm. Strength: Strong. Texture: Smooth, glabrous. Color, young stems: N186C. Color, mature stems: 176B to 176C; axial stripes, 176D.

*Foliage description.*—Arrangement: Alternate, simple. Length: About 3.7 cm. Width: About 2.4 cm. Shape: Elliptic to ovate. Apex: Sharply apiculate. Base: Attenuate. Margin: Spinose, about seven spines on each side. Venation pattern: Pinnate. Texture, upper and lower surfaces: Smooth, glabrous; thick and leathery. Color: Developing foliage, upper surface: Center, 147A; random blotches, 189A and 145C; margins, 150D. Developing foliage, lower surface: Center, 147C; margins, between 150D and 4C. Fully expanded foliage, upper surface: Center, 147A; random blotches, 189A and 191A; margins, between 150D and 4C; venation, 144A; spine apices, 200A. Fully expanded foliage, lower surface: Center, 147B; random blotches, 147C and 148C; margins, 154D; venation, 148A, towards the base, N186C. Petiole: Length: About 5 mm. Diameter: About 1.5 mm. Texture, upper and lower surfaces: Smooth, glabrous. Color, upper and lower surfaces: Between 175A and 176A.

Flower description:

*Flower arrangement and appearance.*—Single cruciform flowers arranged in axillary compound cymes. Freely flowering habit; about 15,000 flowers develop per plant during the flowering period.

*Natural flowering season.*—Plants of the new *Ilex* typically flower during the early spring in The Netherlands. Flowers not persistent.

*Flower longevity.*—Individual flowers last about five days on the plant.

*Fragrance.*—Very faint; sweet, pleasant.

*Inflorescence height.*—About 6 cm.

*Inflorescence diameter.*—About 8 cm.

*Flower diameter.*—About 7 mm.

*Flower depth.*—About 3.5 cm.

*Flower bud.*—Length: About 2 mm. Diameter: About 1.8 mm. Shape: Obovate. Color: 184A to 184B; towards the base, 155B to 155D.

*Petals.*—Arrangement: Single cruciform flower form; single whorl of four petals fused at the base. Length: About 3 mm. Width: About 3 mm. Shape: Broadly elliptic to orbicular. Apex: Rounded. Margin: Entire. Texture, upper and lower surfaces: Smooth, glabrous. Color: When opening and fully opened, upper surface: 184C to 184D; towards the base, 155D. When opening and fully opened, lower surface: 184A to 184B; towards the base, 155D.

*Sepals.*—Arrangement: Four fused in a single whorl; calyx, campanulate. Length: About 1.7 mm. Width: About 1.5 mm. Shape: Deltoid. Apex: Broadly acute. Texture, upper and lower surfaces: Smooth, glabrous. Color: Immature, upper and lower surfaces: 176B to 176B. Mature, upper and lower surfaces: 176B to 176C.

*Peduncles.*—Length: About 1 mm. Diameter: About 1 mm. Angle: About 30° from lateral branch axis. Strength: Strong. Texture: Smooth, glabrous. Color: Between 175A and 176A.

*Pedicels.*—Length: About 1 mm. Width: About 1 mm. Angle: About 90° from vertical. Strength: Moderately strong. Texture: Smooth, glabrous. Color: Between 155A and 157D.

*Reproductive organs.*—Androecium: Quantity per flower: About four. Filament length: About 3 mm. Anther shape: Reniform. Anther length: About 1.5 mm. Anther color: 4D. Pollen amount: Moderate. Pollen color: 8B. Gynoecium: No female reproductive structures observed.

*Seed/fruit.*—Seed and fruit development have not been observed.

Garden performance: Plants of the new *Ilex* have been observed to have good garden performance and to be tolerant to rain and wind. Plants of the new *Ilex* are hardy to USDA Zone 6 and tolerate high temperatures up to 35° C.

Disease/pest resistance: Plants have not been observed to be resistant to pathogens and pests common to *Ilex*.

It is claimed:

1. A new and distinct cultivar of *Ilex* plant named 'Casanova' as illustrated and described.

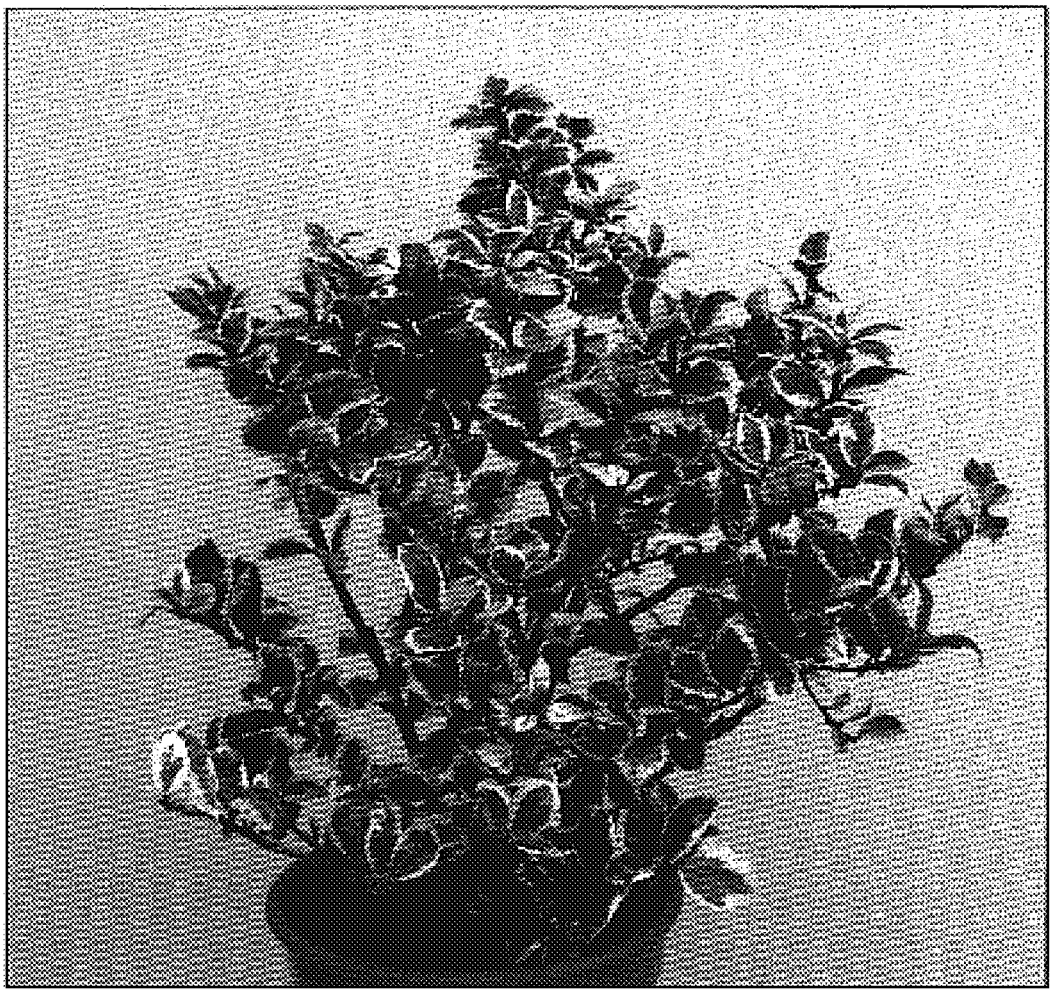

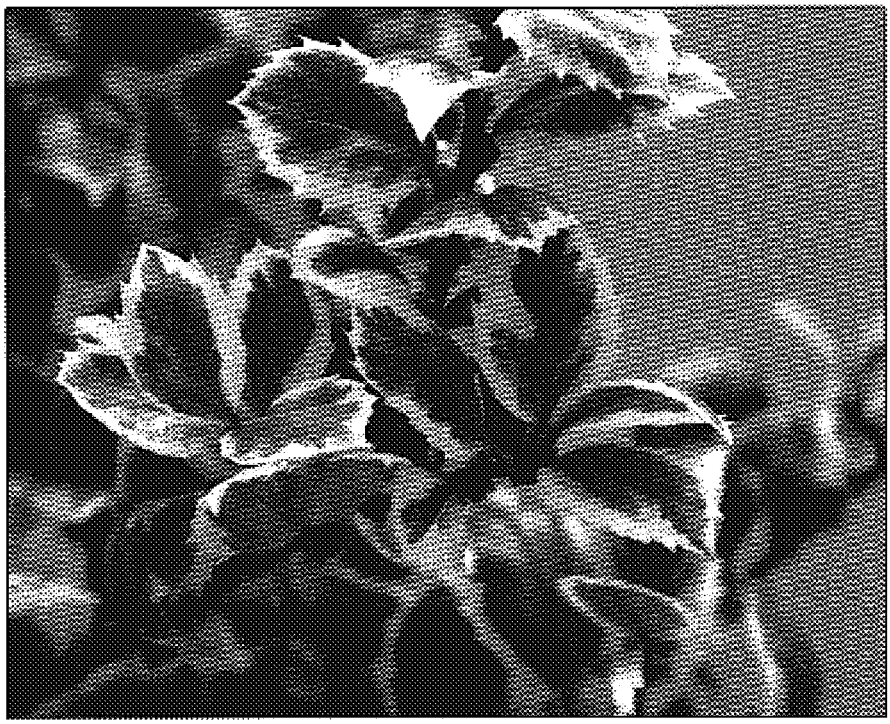
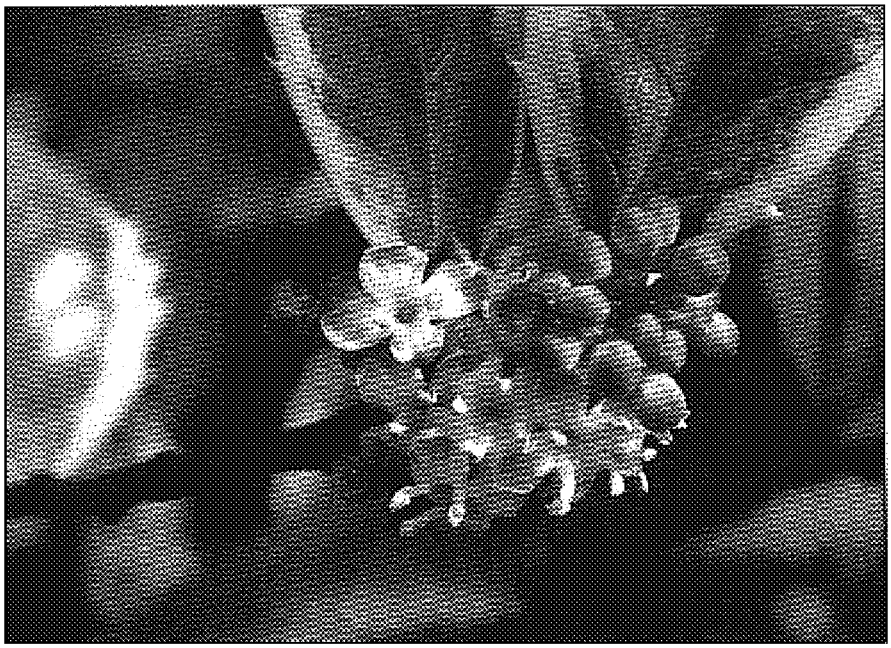

* * * * *